(12) United States Patent
Saxena et al.

(10) Patent No.: US 6,214,849 B1
(45) Date of Patent: Apr. 10, 2001

(54) USE OF NICORANDIL IN TREATMENT OF SEXUAL DYSFUNCTION OR FOR ENHANCEMENT OF SEXUAL FUNCTION IN MAMMALS INCLUDING HUMANS

(75) Inventors: Ajit Saxena, Uttar Pradesh; Dhananjay Sadashiv Bakhle, Mumbai, both of IN (US)

(73) Assignee: Lupin Laboratories Limited, Mumbai (IN)

(*) Notice: Subject to any disclaimer, the term of this patent is extended or adjusted under 35 U.S.C. 154(b) by 0 days.

(21) Appl. No.: 09/326,052

(22) Filed: Jun. 4, 1999

(30) Foreign Application Priority Data

Apr. 29, 1999 (IN) .......................................................... 325//99

(51) Int. Cl.[7] ........................ A61P 15/10; A61K 31/4406
(52) U.S. Cl. ............................................. 514/355; 514/906
(58) Field of Search .................................. 514/355, 906, 514/356

(56) References Cited

U.S. PATENT DOCUMENTS

| 4,801,587 | 1/1989 | Voss et al. | 514/248 |
| 5,565,466 | 10/1996 | Gioco et al. | 514/280 |
| 5,708,031 | 1/1998 | Scott | 514/573 |

FOREIGN PATENT DOCUMENTS 9428902   5/1994   (WO).

OTHER PUBLICATIONS

Stipp, D., et al. "The Selling of Impotence" *Fortune*, No. 5, pp. 69–76 (Mar. 16, 1998).
Brindley, G.S., Br. *Journal of Pharmacology*, vol. 87, No. 3 (Mar. 1986), Abstract.
Hedlund, P., et al. "Effects of Nicorandil on Human Isolated Corpus Cavernosum and Cavernous Artery" *Journal of Urology*, vol. 151, pp. 1107–1112 (Apr. 1994).
El–Sakka, Ahmed, et al., "Physiology of Penile Erection" *Digital Urology Journal*, (http://www.duj.com/Article/Lue-.html) 1996.
Fovaeus, M., et al., *Journal of Urology*, vol. 138 (5) p. 1267–1272 (Nov. 1987) (Abstract).
Kerfoot, W.W., et al., *Journal of Urology*, vol. 150(1) p. 249–252, No. 5, (Jul. 1993), (Abstract).
Bolayir, K., et al.,*Acta Chir. Hung*, vol 34, No. 3–4, p. 253–254 (1994) (Abstract).
Kroner, B.A., et al.,*Annals of Pharmacother.*, vol. 27, No. 11 p. 3129–1332 (Nov. 1993) (Abstract).
MacGregor, M.S. et al., *Nephron*,vol. 74, No. 3, p. 517–521 (1996) (Abstract).
Kim, J.J., et al., *Int. Journal of Impotence Res.*, vol. 10, No. 3 p. 145–150 (Sep. 1998) (Abstract).
Sogari, P.R., et al., *Journal of Urology*, vol. 158, No. 5 p.1760–1763 (Nov. 1997) (Abstract).
Adsan, O., et al., *Arrch. Ital. Urol. Androl.*, vol. 69, No. 3 p. 151–153 (Jun. 1997) (Abstract).

*Primary Examiner*—Edward J. Webman
(74) *Attorney, Agent, or Firm*—Ladas & Parry

(57) ABSTRACT

The present invention discloses the use of nicorandil in treatment of male impotency and female sexual dysfunction. Nitric ester of N-(2-hydroxyethyl) nicotinamide or nicorandil, as it is better known is known as a drug for treatment of circulatory diseases. It is a pyridine derivative. Several clinical tests performed on male patients suffering from impotency including severe penile erectile dysfunction or female patients suffering from female sexual arousal dysfunction consistently showed excellent results. There was not a single instance of any of side effects or other symptoms of toxicity or deaths due to myocardial infarctions as was the case with other drugs including pyrazolopyrimidones compounds.

22 Claims, 2 Drawing Sheets

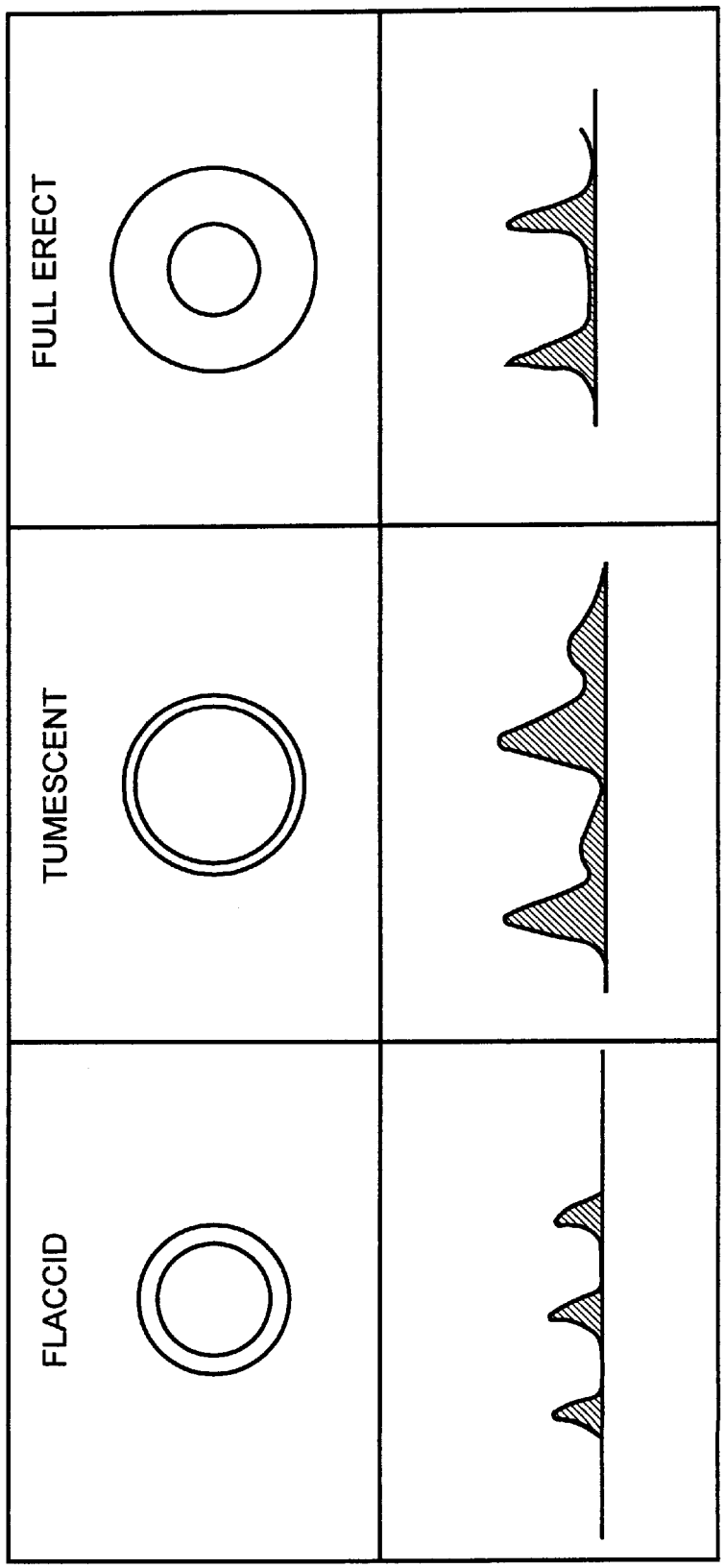

USE OF NICORANDIL IN TREATMENT OF SEXUAL DYSFUNCTION OR FOR ENHANCEMENT OF SEXUAL FUNCTION IN MAMMALS INCLUDING HUMANS

FIELD OF THE INVENTION

The present invention relates to the use of nitric ester of N-(2-hydroxyethyl) nicotinamide in the treatment of impotence in animals, including humans. More particularly, the present invention relates to the use of N-(2-Hydroxyethyl) nicotinamide, commonly referred to as Nicorandil in the treatment of penile erectile dysfunction in males and sexual arousal disorder in females.

BACKGROUND OF THE INVENTION

Impotence in males is normally defined as the inability to copulate including inability to achieve penile erection or ejaculation or both. More particularly, impotence in males is the inability to achieve and/or maintain penile erection sufficient for intercourse. Male impotence is quite prevalent in India and the world over, the incidence being higher in higher age groups. It is estimated that about 7% of the male population in the age group of 18 to 50 years are impotent, the incidence being much higher in the males in the age group of from 55 to 80 years. In the USA, alone it has been estimated that over 10 million males suffer from impotence due to erectile dysfunction, which in majority of them is because of organic rather than psychogenic reasons. In India the figures are considerably higher, given the population and the number of cases that go unreported. In the remaining, psychogenic etiology is believed to be the cause of dysfunction.

Female sexual arousal dysfunction (FSAD) is the inability of the female to be sexually aroused, clitoral erectile dysfunction, inability to copulate and failure to achieve orgasm.

The most common organic diseases responsible for male impotence and sexual dysfunction in females are hypertension, coronary artery disease and diabetes. Another major factor responsible for male impotence is the contractility of the smooth muscle within the corpus cavernosum penis and penile arteries that impede the modulation of penile blood flow by physiological regulators. In the females, the sexual dysfunction is attributable to lack of blood flow in the vaginal area, particularly, the clitoral tissues, which causes clitoral erectile dysfunction, decreased sexual stimulation, dryness and lack of lubrication and pain during intercourse. A similar mechanism, i.e., increased contractility of smooth vascular muscle impedes the modulation of flow of blood in coronary arteries of patients suffering from hypertension or diabetes.

Several other causes for male impotency and female sexual arousal dysfunction have also been studied and reported. Most common amongst them include disorders of endocrine glands such as testicular failure and hyperprolactenemia in males, adverse effects of several drugs such as antidepressants, antihypertensives, anticholinergics, antipsychotics, drug abuse and drug addiction, nicotine abuse, penile and vaginal diseases, neurological diseases, anterior temporal lobe lesions, diseases of the spinal cord and vascular diseases.

Male penile erectile dysfunction has been the subject of greater study than female sexual arousal dysfunction. Vascular diseases such as essential hypertension, aortic occlusion, atherosclerotic occlusion, venous leak and diseases of sinusoid spaces often result in male impotence.

Disorders such as essential hypertension, coronary artery disease and diabetes involve an increase in smooth muscle tone, which limit modulation of blood flow in the vital organs and vascular bed. In U.S. Pat. No. 5,658,936, granted to Kifor and Williams, it is suggested that an imbalance between locally produced Angiotensin II and nitric oxide (NO) leads to an inappropriate tone of vascular smooth muscle resulting in increased blood pressure and altered regional blood flow.

Both vascular and ccp smooth muscles are contracted by angiotensin II. However, this peptide is not believed to be an important regulator of penile blood blow. In fact, it is widely believed that antihypertensive agents, such as ACE inhibitors and angiotensin II antagonists cause sexual dysfunction in males.

While several studies have been conducted to link antihypertensive agents with erectile dysfunction, the results have not been conclusive, but rather, inconsistent. Some drugs which are reported to cause impotence in one case have been reported to be useful in the treatment of impotence in another case.

Some studies have, determined that ACE inhibitors did cause impotence. [Wallcy. T., et al, Adverse Effects of Captopril in Hospital Outpatients with Hypertension, Post Grad. Med. Journ. 1990, 66: 106–109]. Others have shown that ACE inhibitors such as captopril do not show any effect on improving impotence. [Croog et al, Sexual Symptoms in Hypertensive Patients, Arch.Intern.Med 148: 788–794, (1988), Suzuki et al, Effect of First-line Antihypertensive Agents on Sexual Functions and Sex Harmones, J of Hypertension, 6:S649–S651 (1988)]

Several therapies have been formulated, recommended and employed for treatment of penile erectile dysfunction. Common therapies include treatment with androgens, injections into corpus cavernosum of smooth muscle relaxants such as papaverine, phentolamine, phenyl benzamine, prostaglandin $E_1$ etc. Several mechanical devices such as those employing vacuum to produce erection and clips at the base of the penis to restrict and prevent venous return have also been suggested. While injections have been most successful in 70 to 95% cases, self injection is extremely cumbersome and more often than not, quite painful. Its side effects include penile fibrosis and priapism.

Towards avoiding the aforesaid drawbacks, U.S. Pat. No. 5,658,936 suggests a therapy, which could be administered systemically. The method disclosed in this patent involves treating patients having erectile dysfunction with renin-angiotensin system inhibitor particularly selected from the group consisting of angiotensin II antagonist, an ACE inhibitor or a renin inhibitor.

In an alternative approach, WO 94/28902 of Pfizer Limited teaches use of pyrazolopyrimidones for treatment of impotence. This patent also aims to overcome disadvantages of treatment by direct injection into the penis. This patent recognizes that while several drugs have been shown to induce penile erection, they are only effective after direct injection into the penis, e.g. intraurethrally or intracavernosally (i.c). These, however, are not approved for erectile dysfunction.

The above patent specification recognizes that potassium channel openers (KCO) and vasoactive intestinal polypeptide (VIP) have also shown to be active i.c., but costs and stability issues have impeded further research thereon.

As an alternative to i.c. mode of administration, application of glyceryl trinitrate (GTN) patches on the penis have been found to be effective. However, it is seen that these patches not only produce undesirable side effects in the user but also in the partner.

Various penile prostheses have also been suggested but since many of the potential users already have problems such as diabetes, there is a risk of infection and ischaemia.

Accordingly, WO 94/28902 teaches the new use of a known drug pyrazolopyrimidones for treatment of impotence. According to this publication, pyrazolopyrimidones compounds have been unexpectedly found useful in the treatment of erectile dysfunction. The greatest advantage of these compounds is that these may be administered orally, thereby obviating all the drawbacks associated with i.c. administration. Test results conducted on dogs and rats with dosages up to 3 mg/Kg, both intravenously (i. v.) and orally (p. o.) have apparently not shown any adverse acute toxicity and in mouse, even after doses of up to 100 mg/Kg, i. v., no deaths occurred.

Recent studies have however, shown that pyrazolopyrimidones compounds, particularly sildenafil citrate, are liable to be abused not only by males with erectile dysfunction, but also by those without any apparent dysfunction to improve erectile function. Some deaths by myocardial infarction due to over dose of these compounds have been reported. Worse still further deaths were reported which were not attributable to overdose. In fact, in the late March through mid-November 1998, during which more than six million out patients prescriptions, representing more than fifty million tablets were dispensed, the US FDA received reports of 130 US patients who died after having been prescribed this drug. Excluded from this were reports of 55 foreign patients, 35 with unverifiable information (from hearsay, rumor, the media, or unidentifiable reporters), and 22 with unconfirmed sildenafil use. Assuming even 1% truth in the excluded information, the number of deaths are quite large to cause concern.

Hence, there is a strong need for an alternative therapy for a substance having the advantages of the aforesaid compounds without its associated risk.

Over the last few decades, number of theories have been postulated to describe the physiology of erection to understand the role of various factors that may affect the normal functioning. The most important breakthrough has been the identification of nitric oxide (NO) as the major neurotransmitter involved in erection.

Haemodynamics and Mechanism of Erection

The penile erectile tissue, especially the cavernous smooth musculature and the smooth muscles of the arteriolar and arterial wall play a crucial role in the erectile process. In the flaccid state, these smooth muscles are tonically contracted by the sympathetic discharge, allowing only a small amount of arterial flow for nutritional purposes. Sexual stimulation causes the discharge of parasympathetic cavernous nerve terminals activating cholinergic receptors resulting in increased production of nitric oxide. Nitric oxide diffuses across the cell membrane into smooth muscle cells activating guanylate cyclase generating cyclic GMP (cGMP). cGMP depletes intracellular calcium inducing smooth muscle relaxation. Relaxation of the smooth muscle leads to following cascade of events.
1. Dilatation of arteries and arterioles increasing the blood flow.
2. Trapping of incoming blood by expanding sinusoids.
3. Compression of venous plexuses reducing the venous outflow.
4. Increase in intracavernous pressure raising the penis to its erect state.
5. Further increase in the pressure to hundreds of mm. of mercury with contraction of ischiocavernous muscles producing rigidity.

The restoration of flaccid stage (detumescence) occurs in three stages.
1. Transient increase in intracorporeal pressure, marking the beginning of smooth muscle contraction against a closed venous system.
2. Slow pressure decrease coinciding with slow reopening of venous channels with resumption of basal level of arterial flow.
3. Fast pressure decrease and restoration of full venous flow.

Some studies have been conducted on the effect of nicorandil on isolated human corpus cavernosum and cavernous artery. This study recognizes that nitric oxide (NO) released from nonadrenergic-noncholinergic (NANC) nerves seem to be the principal mediator of the relaxation of penile erectile tissues necessary for the reaction. By producing hyperpolarization, K+ channel openers are effective in relaxing isolated penile erectile tissue and can produce erection when injected intracorporeally into animals. Nicorandil is classified as a K+ channel opener but it also acts as a donor of NO. [Hedlund. P, et al., Therapy Recommendations for Adverse Effects of Viagra and nitrates (NO-donors). Effects of Nicorandil on Human Isolated Corpus Cavernosum and Cavernous Artery, J. Urol 1994, April; 15(4): 1107–13]. In this paper, hereinafter referred to as Hedlund's paper for convenience, effects of nicorandil on human isolated corpus cavernosum (CC) and deep cavernous artery (Acc) were compared with those of cromakalim (K+ channel opener) and SIN-1 (NO donor). Nicorandil produced a concentration dependent relaxation of CC and Acc preparations. The relaxation obtained at the highest nicorandil concentration used (10(−4)M.) were 75+/−3% and 66+/−4% in CC preparations contracted by nonadrenaline and endothelin-1, respectively. The corresponding effects in Acc preparations were 70+/−14% and 73+/−5%. Glibenclamide (blocking ATP-dependent K+ channels) significantly reduced the nicorandil induced relaxation in CC, but not in Acc. Methylene blue (believed to block soluble guanylate cyclase) reduced nicorandil's relaxant effect in CC, although statistical significance was not obtained. NG-nitro-L-arginin 10(−4)M. (NO synthase inhibitor) did not significantly influence the effect of nicorandil on pre-contracted preparation in either tissue. In CC preparations contracted by electrical field stimulation, nicorandil and cromakalim concentration dependently inhibited the responses. This effect was significantly counteracted by glibenclamide. These studies then concluded that nicorandil is effective in relaxing human CC chiefly by its K+ channel opening action, and to some extent by its ability to release NO. For nicorandil's relaxing effect on Acc, ATP dependent K+ channels seem to be of limited importance.

However, the above studies were not conducted on any live animal or human, let alone any animal or human with sexual dysfunction or penile erectile dysfunction. The authors merely hypothesise that if effective in impotent patients, the drug may represent a new, interesting approach to the treatment of erectile dysfunction. This is hardly surprising, since, the object of these studies were to compare the mechanism of action of these drugs and not study their effect or efficacy in the treatment of penile erectile dysfunction. Besides, this paper only addresses intracavernous mode of administration and not oral route at all.

Thus, the above studies were not conclusive because they were never tried out on impotent patients. Besides, in vitro tests do not always show results identical to in vivo studies, leave alone predict workable results for in vivo use. In fact, extrapolation of such in vitro experiments to living human beings is fraught with different results on many occasions. (e.g. the use of histamine to cause contraction of smooth muscles). This is more so in case of nicorandil due to its peculiar mechanism of action. It increases the level of cGMP in the corpus cavernosum through its NO donor effects. While, this may show demonstrable effects in an isolated tissue, in a live human this cGMP will be exposed to the degradation pathway that is continuously in operation. There is an auto feedback mechanism that regulates the secretion and metabolism of such neurotransmitters to maintain a balance. Therefore, it is mandatory that the effects of any such drug be tested in live human systems to be able to make any hypothesis. If such an extrapolation were possible, then many chemicals, which are known to produce alteration in the functioning of isolated tissues would have found clinical use for various conditions in clinical practice.

In fact, the prior art is replete with literature which establish that (1) there is no correlation of in vitro results with human corporus cavernosus tissue with therapeutic use by oral route and (2) in vitro results are not routine methods for assessing oral efficacy. U.S. Pat. No. 5,565,466 of Zorgniotti et al discusses the lack of success of phentolamine as an oral pill since oral compounds were too quickly broken down by the stomach and the liver to act on the penile arteries. At the same time, increasing the dosage to compensate loss by metabolic breakdown caused lowering of blood pressure to dangerous levels. Finally, sublingual administration by lacing lollipops with phentolamine was successful. This was the first non cavernous use of a drug for treating erectile dysfunctions.

U.S. Pat. No. 5,565,466 was filed in 1993, about the same time Hedlund's paper was submitted for publication. During that time, non cavernous use of drugs for treating sexual dysfunction was virtually unknown. Therefore, not only there was no correlation between intracavernous route and oral route, but the question of oral route for administration of drug itself was never contemplated by Hedlund et al. This is clear from WO 94/28902 of Pfizer referred to above, which clearly states that "although many different drugs have been shown to induce penile erection, they are only effective after injection into the penis, i.e., intraurethrally or intracavernosally (i.c.), and are not approved for erectile dysfunction". Thus, a different route of administration of a drug, which has been used in intracavernous form earlier, may still represent a novel and nonobvious approach, for instance alprostadil and phentolamine. In fact, topical use of prostaglandins and phentolamine which were known for their intracavernous use are the subject matter of U.S. Pat. Nos. 5,708,031 and 4,801,587 respectively.

There are various other publications, which amply demonstrate that an in vitro efficacy of a drug in the relaxation of penile erectile tissue cannot be translated into its clinical efficacy for erectile dysfunction. In fact, several drugs, which showed good relaxant effect in vitro, caused impotency, instead of relieving it in clinical practice. Similarly, an effective drug like sildenafil, which has proven efficacy in hundreds of thousands of patients produces no relaxant effect on the isolated human corpora cavernosa in in vitro experiments.

Hedlund et al have also studied the effects of calcium channel blockers on isolated human penile erectile tissue. (Fovaeus M., Anderssen K. E. and Hedlund H., Journal of Urology, [November 1987] 138 (5) p 1267–1272). While discussing the results, the authors have clarified that though calcium channel blockers can depress the noradrenaline induced contractions of the corpora cavernosa, they may not be as effective as a therapeutic principle as alpha-blockers. Thus, the same authors have admitted that isolated tissue effect may not even correlate with therapeutic use.

Calcium channel blockers relax the cavernosal smooth muscle and it was suggested that they possess potential as intracavernous agents for the treatment of erectile dysfunction. It was also suggested that verapamil was the best candidate for such use. (Kerfoot W. W., et al, Journal of Urology (July 1993) 150[1] p 249–252). Subsequent studies concluded that this combination therapy including verapamil is reliable, well accepted in erectile dysfunctions. (Bolayir K. and Goksin N., Acta Chir. Hung (1994) 34 (3–4) p 253–256)

At the same time, another study reported that veramapil has no effect in sexual function in clinical use. (Kroner B. A., et al, Annals of Pharmacother (November 1993) 27 (11) p 1329–1332)

Similarly ACE inhibitors have been shown to produce smooth muscle relaxation in isolated tissue but in clinical use they have been even linked with impotence. (McGregor M. S., et al, Nephron (1996) 74 (3) p517–521).

Acetylcholine is a known contractor of smooth muscle. However, on the isolated smooth muscle preparations of corpus cavernosum, it produces a relaxation. (Kim J. J., et al, Int. Journal of Impotence Res. (September 1998) 10 (3) 145–150). Despite this fact, atropine, which is an anti-acetylcholine drug does not worsen impotence. On the contrary, it has been tried out to treat impotence. At the same time, other studies show that there is no special advantage in adding atropine to other vasorelaxants administered by intracavernous route. (Sogari P. R., et al, Journal of Urology (November 1997) 158 (5) p 1768–1769). Therefore, it is clear that the in vitro relaxation effects of acetylcholine on the corpus cavernosum has no implications on the in vivo use of atropine, which is a blocker of acetylcholine. The same atropine is used to block the effects of acetylcholine at other sites for its therapeutic use e.g., to prevent vaso-vagal shock in patients after operation.

In conclusion, it is quite clear that in vitro experiments with a particular drug on isolated human corpus cavernosus tissue are unpredictable as far as the efficacy of the same drug for use in the treatment of erectile dysfunction is concerned. Even live biopsy of the patients has shown frustrating results for predicting etiology of erectile dysfunction (Adsan O., et al, Arch. Ital. Urol. Androl. (June 1997) 69 (3) p 151–153). In fact, if sildenafil citrate was to undergo the method of evaluation prescribed in the Hedlund paper, it would not have shown any effect since it does not directly relax the isolated smooth muscle of corpora cavernosa.

The reason why in vitro studies conducted by Hedlund et al will have no clinical value especially, in the treatment of erectile dysfunction by the oral method suggested in the present application will be clear from the following:

The statement in Hedlund's paper "If effective, in impotent patients, the drug may represent a new, interesting approach to the treatment of erectile dysfunction refers to the intracavernous route of administration of nicorandil. This conclusion is inescapable considering the fact that question of oral administration does not arise in in vitro experiments involving penile tissues and from the introduction in the paper which states "By injecting vasorelaxant drugs in the corpus cavernosum, erection may be produced in patients of erectile dysfunction". (Hedlund, Journal of Urology [April 19941], Vol 151 p 1107–1113 referred to above). The introduction highlights the problems such as priapism faced with intracavernous use of drugs such as papaverine, phentolamine and prostaglandins and contemplates safer alternatives like nicorandil. Obviously, the suggestion is only for intracavernous and not any other mode of use of nicorandil. The introduction also emphasises that "before any drug is used in the treatment of erectile dysfunction, it is desirable to have information on its effects on penile erectile tissues, particularly, human tissue. This confirms that the suggested use of nicorandil is by intracavernous route since, in vitro effects on human tissue may correlate with intracavernous injection but are not known to correlate with systemic use.

Hedlund's paper also compares intracavernous use of pinacidil and cromakalim. This paper also makes a direct reference to another study in monkeys where pinacidil was injected intra corporeally (in corpora cavernosa). This effect of pinacidil given by intracorporeal injection has been compared with the action of nicorandil on isolated penile erctile tissue. Hedlund also refers to a paper by Hellstrom who had injected nicorandil intracorporeally into an anaesthetized cat and compared the results to those achieved with a standard drug combination which was used therapeutically (papaverine, phentolamine and prostaglandin) by intravenous injection. It is significant to note that the in the last sentence of his paper, Hedlund states that "further studies seem necessary to evaluate beneficial effects of nicorandil in the treatment of erectile dysfunction". This makes it clear that even in respect of intracavernous route of administration, further studies, in humans, are necessary before the beneficial results of nicorandil for treatment of erectile dysfunction are evaluated.

On this background there is no study whatsoever to prove unequivocally that nicorandil could be used in human beings for the enhancement of erectile function in males and sexual arousal in females.

OBJECTS OF THE INVENTION

It is therefore, an object of the present invention to provide a compound for use in the treatment of sexual dysfunction such as penile erectile dysfunction and female sexual arousal dysfunction which does not have the side effects of the prior art.

It is another object of the present invention to provide a compound for use in the improvement of sexual function such as penile erectile function and female sexual arousal which does not have the side effects of the prior art.

It is yet another object of the present invention to provide a compound for use in the treatment of sexual dysfunction or in the improvement of sexual function and which does not have the side effects of the prior art and which is easy to administer and employed in small dosages.

It is a further object of the present invention to provide a pharmaceutical composition for use in the treatment of sexual dysfunction or in the improvement of sexual function and which does not have the side effects of the prior art and which is easy to administer and employed in small dosages.

It is another object of the present invention to provide a method for the treatment of sexual dysfunction in mammal, particularly humans and for enhancement of sexual function in mammals, particularly, humans.

These and the other objects of the present invention are achieved by use of the compound Nicorandil having the general formula:

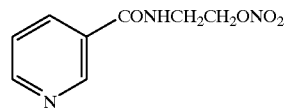

BRIEF DESCRIPTION OF THE FIGURES

FIG. 1 shows a cross section of penis along with the flow pattern in flaccid condition:

FIG. 2 shows a cross section of penis along with the flow pattern in tumescence.

FIG. 3 shows the cross section of penis along with the flow pattern in its full erect condition.

SUMMARY OF THE INVENTION

Figure 4:
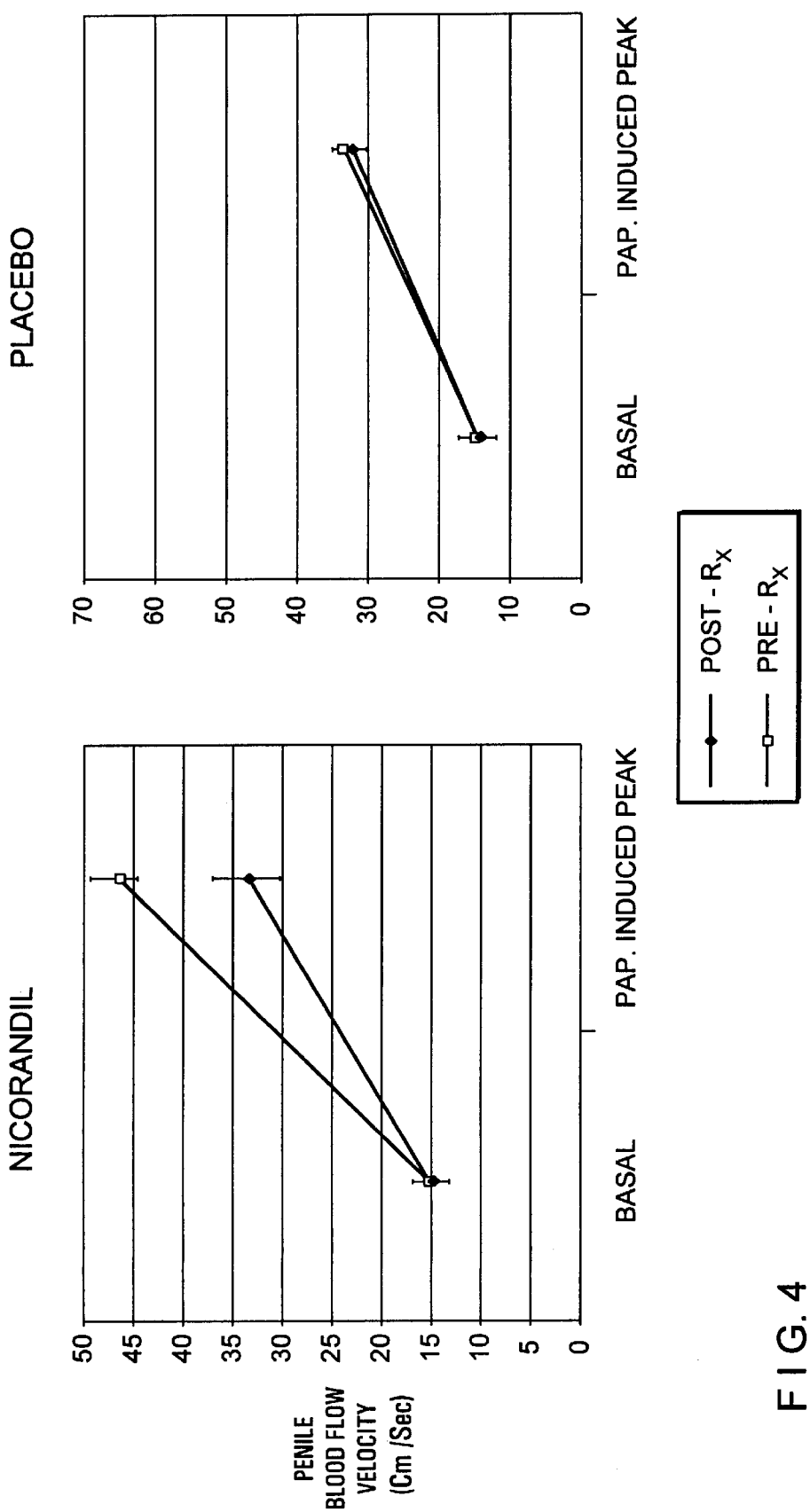
FIG. 4 shows a graph comparing changes in penile blood flow when treated with nicorandil and placebo respectively.

The applicants have now discovered that nicorandil is most surprisingly and remarkably effective in treatment of male impotency when used in specific dosages of 5 to 20 mg preferably, 5 to 10 mg, more particularly 5 mg on humans and animals suffering from erectile dysfunction. Several clinical tests performed using oral route of administration, on male patients suffering from impotency including severe penile erectile dysfunction consistently showed excellent results. Besides, there was not a single instance of any of side effects or other symptoms of toxicity or deaths due to myocardial infarctions as was the case with other drugs including pyrazolopyrimidones compounds.

Nitric ester of N-(2-hydroxyethyl) nicotinamide or nicorandil, as it is better known, is a well known drug for treatment of circulatory diseases. It is a pyridine derivative of the formula:

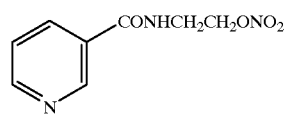

The above compound is the subject of U.S. Pat. No. 4,200,640 of Nagano et al. This patent describes in detail the activity of the above-mentioned compound in various circulatory diseases such as coronary vasodilatory action, antihypertensive action, anticoagulative action, and peripheral vasodilatory action. The Patent also refers to its various uses e.g. for treating ischemic heart disease, as antihypertensive drug, as cerebral and renal vasodilator but there is no reference or even a suggestion in the patent to the possibility of its use as an anti impotence drug. In fact, there is nothing in the entire patent document to indicate that any of the subjects treated by this drug showed any improvement in penile erectile function or was cured of any erectile or sexual dysfunction. To be more specific this patent document does not address the problem associated with impotency at all.

It has now been unexpectedly found that nicorandil compounds when administered non invasively, particularly orally, are remarkably useful in the treatment of erectile dysfunction. Best results are obtained when administered orally, in the form of tablets thereby obviating the disadvantages associated with i.c administration.

As stated above, the compound of formula (I), its preparations, and its uses in circulatory diseases have been described in U.S. Pat. No. 4,200,640 granted to Nagano et al, and the contents thereof are incorporated herein by reference. This patent also teaches the results of in vivo studies conducted to demonstrate the effects of nicorandil in coronary blood flow, systemic blood pressure, heart rate and variant angina pectoris.

Currently, nicorandil is quite commonly used for treatment of Angina. In patients of Angina Pectoris it is orally administrated in a dosage of 10 mg. twice daily to be increased up to 40 mg twice daily. (Drugs:1992). It has been observed that exposure to nicotine and tar containing cigarette smoke delays the absorption of nicorandil from the gastrointestinal tract and therefore, it is advisable to give nicorandil by intravenous route for patients of unstable angina. (Drugs; 1992).

In vivo Investigations with oral route of administration were carried out for the first time by the present inventor for studying the effects of nicorandil in human corpus cavernosum tissues. The relaxation of the corpus cavernosum tissue and the consequent penile erection is, it is believed, due to the action of nicorandil on the erectile dysfunction by central and local actions. The drug works through many mechanism that operate in vivo and which cannot be predicted by experiments on isolated human penile erectile tissues. Two of these mechanism require use of whole and live animal. This is due to the fact that penile erection is on of the most complex phenomenon involving multiple systems in simultaneous operation. In short, it requires the following nervous pathways and neurotransmitters to effect erection. The nervous pathways involved are:

Automatic nerves:
Sympathetic pathway originating form 11th thoracic to 2nd lumbar spinal segments;
Parasympathetic pathways arising from neurons in the intermediolateral cell columns of the second, third and fourth sacral spinal cord segments;
Somatic nerves originating at the sensory receptors in the penile skin, glans, urethra and within corpus cavernosum.

Neurotransmitters involved are:
Peripheral such as noradrenaline, endothelin, acetylcholine, thromboxane A2, prostaglandin F2a, leukotrienes and nitric oxide.
Central such as Dopamine, noradrenaline, sertonin and oxytocin.

All these work in an orchestrated manner in an intact human to produce erection. Thus, in vitro experiments using a small strip of human cavernous tissue cannot correlate with clinical and therapeutic use in humans. Moreover, the therapeutic use presupposes an erectile dysfunction in patients and therefore, existence of an abnormality due to varying etiology which is normally vasogenic in origin and thus has no correlation with in vitro use in a normal isolated tissue.

Central Action

By increasing nitric oxide synthase activity in the paraventricular nucleus of the hypothalamus, possible in the cell bodies of oxytocinergic neurons projecting to extrahypothalamic brain areas nicorandil can induce penile erection. It has been demonstrated that NOergic neurons play an important role in stimulating the release of lutenizing hormone releasing-hormone (LHRH), prolactin-RH's, particularly oxytocin. NO stimulates the release of LHRH, which induces sexual behaviour, and causes release of LH from the pituitary gland.

The intra hypothalamic pathway by which NO controls LHRH release is as follows: glutamergic neurons synapse with noradrenergic terminals in the median basal hypothalamic region, which release nonepinephrine (NE) that acts on alpha 1 receptors on the NOergic neuron to increase intracellular free $Ca^{++}$ which combines with calmodulin to activate NOS. The NOS diffuses to the LHRH terminal and activates guanylate cyclase (GC), cyclooxygenase and lipoxygenase causing release of LHRH via release of cyclic GMP, PGE2 and leukotrienes, respectively.

Paraventricular nucleus of the hypothalamus (PVN) is one of the richest brain areas of NO synthase and also the brain site where dopamine, NMDA and oxytocin act to induce penile erection by activating central NO synthase containing oxytocinergic neurons. The inhibitory effect of NO synthase inhibitors was not observed when these compounds were injected concomitantly with L-arginine, the precursor of NO. Most importantly, NO synthase inhibitors given intraventricularly but not in the PVN actually prevent penile erection induced by ACTH and serotonin 1c agonists, which induce these responses by acting with mechanisms unrelated to oxytocinergic transmission. Dopamine agonists, NMDA and oxytocin increase NO production in the PVN at doses that induce penile erection, as determined by measuring the concentration of NO2- and NO3- in the dialyzate obtained with a vertical probe implanted in the PVN by in vivo microdialysis. NO donors, such as nitroglycerin, sodium nitroprusside and hydroxylamine, induce penile erection indistinguishable from those induced by oxytocin, dopamine agonists or NMDA when injected in the PVN. The NO donor response was prevented by the intraventricular injection of the oxytocin receptor antagonist d(CH2)5-Tyr(Me)-Orn8-vasotocin, indicating that these compounds also induce penile erection by activating oxytocinergic transmission. Finally, guanylate cyclase inhibitors (i.e. methylene blue and LY 83583) and hemoglobin in the PVN do not prevent drug induced penile erection, nor 8-Br-cGMP injected in the PVN induces these behavioral responses, suggesting that the mechanism by means of which endogenous or NO donor derived NO facilitates oxytocinergic transmission to induce penile erection is not related to the activation of guanylate cyclase. Furthermore, since hemoglobin, in spite of its ability to prevent drug induced NO production in the PVN, does not prevent penile erection, it is likely that NO acts as an intracellular, rather than an extracellular modulator in the PVN neurons in which it is formed to facilitate the expression of these behavioral responses.

This shows that the central action of nicorandil is mediated by different mechanisms and transmitters as compared to its local actions.

Local Actions

Stimulating guanylate cyclase leads to increased levels of cGMP. This is known to be mediated by NO donating mechanism.

Hyperpolarisation takes place through opening of ATP-dependant potassium channels. Calcium activated potassium channels are a diverse group of ion channels that share dependence on intracellular calcium for activity. Potassium ions play a dominant role in controlling the resting membrane potential in most excitable cells and in maintaining the transmembrane voltage. It is known that opening of potassium channels shifts the cell membrane potential towards the equilibrium of potassium membrane potential resulting in hyperpolarisation of the cell. Hyperpolarisation of the cell membrane is thought to mediate vasorelaxation by decreasing the level of cytoplasmic calcium as a result of closing voltage-dependant calcium channels in the cell membrane and enhancing calcium efflux via the sodium-calcium exchanger.

It appears that nicorandil has a multi-pronged effect in producing relaxation of the smooth muscle of corporus cavernosus and the deep cavernous vessels. Whether it is the activation of guanylate cyclase through NO donor mechanism or hyperpolarisation through potassium channel opening, nicorandil depletes the calcium stores in the smooth muscle cell causing it to relax.

It has been demonstrated that K+ channel opening and guanylate cyclase stimulation actions are independent pathways that induce additive vasorelaxation. The mechanism of action of nicorandil is dependent on the artery and on the nature of the agonist employed to precontract the artery. The relative efficacy of the K+ channel opening vs. guanylate cyclase stimulation may partially explain the preferential contribution of each mechanism to the relaxant effects of nicorandil. Nicorandil had been shown to relax corpora cavernosal smooth muscle chiefly by its K+ channel opening action and to some extent by its action to release NO. Whereas on the deep cavernous artery, nicorandil produces vasodilatation by guanylate cyclase stimulation.

Mechanism of Action of Nicorandil in Female Sexual Arousal Disorder (FSAD)

In the case of "female sexual arousal disorder", nicorandil is expected to work by its central action through oxytocinergic activation and release of LHRH. Both the hormones have been linked to influence sexual behaviour.

Nicorandil also brings about dilatation of the arteries supplying vagina and the clitoral area. There is some evidence suggesting that the potassium channel opening action seems to be of limited importance, the role of activation of guanylate cyclase may be dominant.

None of the tests conducted on animals or man showed any signs of toxicity or any other side effects.

The method of administration employed was through the oral route. The preferred dosage is 5 to 20 mg of the compound, twice a day although, just one dose of 5 mg one hour prior to intercourse provides excellent short term results. However, in case of patients suffering from any oesophageal disorder or impairment, sublingual or buccal administration may be effectively employed.

For use on animals, normal oral route or buccal route may be employed in a dosage prescribed by the veterinarian depending upon the type and sex of the animal.

DETAILED DESCRIPTION

Accordingly, the present invention provides a method of treating mammals, including humans suffering from penile erectile dysfunction or female sexual arousal dysfunction as the case may be, which comprises administering to said mammal either orally or sublingually or buccally, an effective amount of a compound of formula (I):

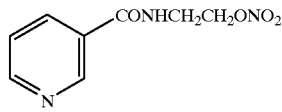

(I)

or a pharmaceutically acceptable salt thereof, or pharmaceutical composition containing either of the above.

The present invention also concerns methods of treating normal mammals including humans to improve their sexual functions.

The pharmaceutical composition may contain an effective amount of a compound of formula (I) or a pharmaceutically acceptable salt thereof in a pharmaceutically acceptable diluent or carrier.

Thus, the present invention also provides a pharmaceutical composition for treating mammals, including humans suffering from penile erectile dysfunction or female sexual arousal dysfunction as the case may be, which comprises an effective amount of the compound of formula (I) or a pharmaceutically acceptable salt thereof in a pharmaceutically acceptable carrier or diluent.

The present invention also provides a method for the treatment of humans to improve penile erection function or female sexual function which comprises administering to said human an effective amount of the compound of formula (I) or a pharmaceutically acceptable salt thereof or a pharmaceutical composition containing either of the above.

Advantages of Nicorandil Over Sildenafil

Sildenafil is a potent inhibitor of cGMP specific phosphodiesterase V. Therefore, it causes elevation of cGMP levels by blocking its degradation. While nicorandil causes the release of nitric oxide and stimulation of guanylate cyclase to elevate cGMP levels. Thus the major difference is that sildenafil blocks the exit of cGMP while nicorandil works at the entry level by pouring out increased quantities of cGMP. There are certain disadvantages of blocking the exit pathway.

Firstly, it can cause priapism, which is the persistence of erection that fails to subside despite orgasm. This adverse effect has been noted with sildenafil use in patients. Since nicorandil does not block exit mechanism, priapism was not observed in the current study despite injection of papaverine.

Secondly, accumulation of CGMP at other sites in the human body can have disastrous effects, because cGMP is a molecular messenger involved in diverse cellular processes. In the normal functioning of retinal photoreceptors, light absorbed by a photopigment causes a photochemical reaction leading to a series of events causing decrease of cGMP in the cytoplasm of the photoreceptor. The vision disturbances (specially "blue-green vision") seen as an adverse effect of sildenafil has been attributed to accumulation of cGMP in the retinal cells. Nicorandil does not have this problem of accumulation due to the exit pathway remaining intact.

During a short period of 9 months, Sildenafil caused 77 deaths in USA alone, due to cardiovascular events (41 with definite or suspected myocardial infarction, 27 with cardiac arrest, 6 with cardiac symptoms and 3 with coronary artery disease). 12 patients had no previous history of heart disease or risk factors. 2 men did not even have sexual activity but died shortly after consumption of sildenafil. In view of these the regulatory agency in USA is evaluating the need for regulatory action against sildenafil.

Thus, currently, sildenafil therapy is avoided in certain groups of patients. Sildenafil is now known to be contraindicated in patients already on nitrates and/or patients with ischaemic heart disease who are susceptible to the haemodynamic side effects of sildenafil. Other major side effects of sildenafil are blue-green vision and priapism. This profile necessitates the need for a safer oral therapy for the treatment of erectile dysfunction and nicorandil fulfills this need perfectly.

The effect of Nicorandil on live humans and its effect on erectile sexual dysfunction was carried out as against earlier studies on corpus cavernosum of frozen penis. Data was collected on the basis of actual studies carried out.

METHODS

The clinical study conducted was a double blind placebo controlled clinical trial comparing nicorandil with placebo in 55 patients of erectile dysfunction. These cases were diagnosed on the basis of history and penile doppler test, which was specially adapted to objectively quantify the improvements of blood flow to the penis. In order to measure effectiveness of test therapy on erectile function in a laboratory setting, a modification of the method was done to quantify the improvements in blood flow. This method incorporated injection of papaverine (30 to 60 mg.) by intracavernous route. The change (if any) in the blood flow due to nicorandil & placebo was measured by penile doppler studies after provocation with papaverine. This method obviated the need for visual sexual stimulation, which is difficult in a laboratory setting and extremely variable.

Subjective Evaluation of Patients

The patients were assessed with respect to their sexual performance in the form of a questionnaire. People who were able to have a satisfactory intercourse on one or more occasions (and were unable to have the same earlier) were classified as responders to the therapy.

Objective Assessment of Patients
Penile Doppler—Intracavernous Injection Test Colour doppler ultrasonic flowmetry method was used for measurement of blood flow to an end organ. This method has been standardized for the diagnosis and monitoring of patients with erectile dysfunction. The method employs measurement of penile blood flow in basal as well as stimulated conditions. The doppler equipment used in the present study was—HP Sonos 2500 with a 7.5 Mhz linear probe.

The method consisted of measuring the velocity of blood flow through the right and left penile arteries in the basal condition i.e. before any stimulants (in this case papaverine) had been administered.

Intracorporeal injection of papaverine, first introduced by Virag and associates in 1984, was found to be a useful diagnostic tool in patients with suspected vasculogenic impotence. This test allows the clinician to bypass the neurogenic and hormonal influences and to evaluate the vascular status of the penis directly and objectively. The papaverine relaxes the penile vascular sinusoids and increases the blood flow in the cavernous arteries. The resultant engorgement of the corpora results in compression of the subtunical venules and decreases penile venous outflow. Therefore, to produce the normal erection, arterial vasodilatation, sinusoidal relaxation, and decreased venous outflow must all occur in response to papaverine.

STUDY PROCEDURE

Informed consent was obtained from each patient prior to the study. All patients were screened for routine medical examination and biochemical investigations to look for any associated medical condition. Detailed clinical history was taken and recorded in all cases. The patients were then subjected to a pre-treatment penile doppler study. This served two purposes, i.e., (1) To select cases of vasculogenic impotence and (2) to form a baseline record for further comparison following treatment.

The basal reading was taken in flaccid condition of the penis in the absence of any stimulants. This reading reflected the resting blood flow velocity through the penile arteries. To provoke an erection without psychological stimulation, papaverine is injected in the corpora cavernosa. Papaverine is a smooth muscle relaxant which produces dilatation of arteries and causes the engorgement of penis. In this study, papaverine in the dosage of 30–60 mg. was administered by intracaverous injection and the response noted.

This papaverine test is usually performed to distinguish cases of vasculogenic from non-vasculogenic causes of erectile dysfunction. This is possible by identifying the flow patterns in various stages of penile erection. The changes in the diameter of the penis and the flow velocity pattern are depicted in the accompanying drawings wherein:

FIG. 1 shows a cross section of penis along with the flow pattern in flaccid condition FIG. 2 shows a cross section of penis along with the flow pattern in tumescence, and FIG. 3 shows the cross section of penis along with the flow pattern in its full erect condition.

FIG. 4 shows a graph comparing changes in penile blood flow when treated with nicorandil and placebo respectively.

The flow patterns can be described in three phases as follows:

1) Basal Level:

In the basal condition (flaccid stage), there is a sharp systolic peak followed by rapid fall during diastole. However, the peak velocity remains within normal limits. (FIG. 1)

2) Plateau phase:

In a normal person, an injection of papaverine will increase the peak velocity. At the same time the diastole becomes prolonged in the shape of a plateau. It is the disappearance of this plateau phase that correlates with the turgidity of penis. (FIG. 2)

3) Vasoconstrictor Phase:

There is a marked increase in the peak systolic velocity and a disappearance of the plateau like diastole. (FIG. 3) This phase corresponds to the rigidity of the penis. In a normal person, the increase in the peak flow velocity over basal flow velocity is three fold or more.

In case of vasculogenic impotence the increase in the peak systolic blood flow velocity has been observed to be less than twice. In addition, there may be a marked prolongation of the plateau phase. This prevents the full development of vaso-constrictor phase, hence the rigidity of the penis.

The penile doppler ultrasonic velocimetry is thus useful to objectively measure even the minor changes in the blood flow through the penis. Hence, it can be used as an excellent model to measure effects of drugs that would modify the hemodynamics of the penis. The drug effects can also be quantified by measuring the extent of increase in the blood flow velocity provoked by papaverine. It has been established that such measurements correlate very well with therapeutic response seen in patients with erectile dysfunction.

STUDY PROTOCOL

Patients of vasculogenic impotence were randomized into 2 groups, (A) Nicorandil and (B) Placebo. Patients in group A received nicorandil in the dose of 5 mg. twice daily for a period of 14 days. Patients in the group B received a matching placebo.

The concept behind continuous administration of nicorandil was to produce adequate biochemical effects in readiness of its required action in presence of psychological stimulation. Based on the proposed mechanism of action it appears that nicorandil does not produce any action without sexual arousal. The low dosage of nicorandil for this indication (as opposed to the therapeutic dosage used in Angina), facilitate continuous action at the target organ without producing any significant side effects.

A subjective and objective assessment was done after 15 days of daily therapy. Side effects if any were noted as also the positive effects other than enhancement sexual function.

RESULTS

DEMOGRAPHIC DATA

The average age of patients in group A (nicorandil group) was 45 years while the average age of patients in group B (placebo group) was 44 years.

Duration of Erectile Dysfunction:

The average duration of erectile dysfunction in group A was around 5 years, whereas in group B was around 4 years.

Associated Diseases:

5 patients in group A and 3 patients in group B had diabetes mellitus. 3 patients in group A and 2 patients in group B had hypertension as an associated condition. The medication history was checked for these patients and drug related causes of impotence were ruled out.

Subjective Assessment:

76% patients who received nicorandil showed success in attaining erections and were able to have satisfactory sexual intercourse (as also corroborated by their partners.) The questionnaire evaluated various qualitative aspects of erectile dysfunction ranging from gradation of erectile response, intercourse satisfaction, orgasmic function and overall satisfaction.

Objective Assessment:

CHANGES IN PENILE BLOOD FLOW

There was at least a three fold increase in the penile blood flow in patients receiving nicorandil as compared to placebo. In the control group, prior to administering placebo, the penile blood flow velocity increased from a mean basal of 13.73 ($\pm 0.92$ SEM) to papaverine induced peak of 32.61 ($\pm 2.07$ SEM) cm/sec. After 14 day treatment with placebo, the values remained very similar. Thus the penile blood flow velocity increased from a mean basal of 13.73 ($\pm 0.92$ SEM) to papaverine induced peak of 33.16 ($\pm 2.07$ SEM) cm/sec. On the contrary, group A, who received nicorandil, showed significant increases in basal to peak flow velocity changes. During pretreatment period, the penile blood flow velocity increased from a mean basal of 14.71 ($\pm 0.39$ SEM) to papaverine induced peak of 33.14 ($\pm 1.12$ SEM) cm/sec. Whereas, after a 14 day course of nicorandil the penile blood flow velocity increased from a mean basal of 14.63 ($\pm 0.39$ SEM) to papaverine induced peak of 46.75 ($\pm 1.66$ SEM) cm/sec. These changes in the mean penile blood flow velocity are represented in the graph shown in FIG. 4 of the drawings.

The comparative increase in the blood flow velocity due to papaverine provocation in the placebo group (as calculated from the difference of average flow increase) was only 8%, whereas this increase in the nicorandil group was 89% as shown in the attached tables 1 and 2.

CLINICAL TRIAL OF NICORANDIL

Group A: Nicorandil
Group B: Placebo

| GROUPS | PENILE BLOOD FLOW Cm/sec. | PARAMETERS MEAN | SD | SEM |
|---|---|---|---|---|
| A NICORANDIL TREATED n = 37. | Pre Rx Basal Values | 14.711 | 2.368 | 0.39 |
| | Pre Rx Peak Values | 33.143 | 6.79 | 1.12 |
| | Difference | 18.54 | 5.323 | 0.87 |
| | Post Rx Basal Values | 14.632 | 2.407 | 0.39 |
| | Post Rx Peak Values | 46.746 | 10.1 | 1.66 |
| | Difference | 32.113 | 8.34 | 1.37 |
| B PLACEBO TREATED n = 18. | Pre Rx Basal Values | 13.728 | 3.89 | 0.92 |
| | Pre Rx Peak Values | 33.16 | 8.78 | 2.07 |
| | Difference | 19.439 | 6.63 | 1.57 |
| | Post Rx Basal Values | 13.593 | 3.88 | 0.92 |
| | Post Rx Peak Values | 33.094 | 9.19 | 2.17 |
| | Difference | 19.439 | 6.99 | 1.65 |

SD = Standard Deviation
SEM = Standard Error of the Mean.
n = Number of patients.

STATISTICAL ANALYSIS: Student's T-Test (Two Tailed)

1. Significance of the difference between the basal and peak blood flow values before and after treatment in Group A

| Parameter | DiffPreRx | DiffPostRx |
|---|---|---|
| Mean | 18.54 | 32.113 |
| Variance | 29.536 | 69.564 | t value=12.773 df=36 p<0.005
The means of the two samples are HIGHLY SIGNIFICANT.

2. Significance of the difference in the basal and peak blood flow values before and after treatment in Group B

| Parameter | DiffPreRx | DiffPostRx |
|---|---|---|
| Mean | 19.439 | 19.439 |
| Variance | 44.037 | 48.959 | t value=1.626 E-08 df=17 p=1.
The means of the two samples are NOT SIGNIFICANT.

3. Significance of the differences in peak blood flow in the Nicorandil and Placebo groups.

| Parameters | Nicorandil | Placebo |
|---|---|---|
| Mean | 32.1135 | 19.4388 |
| Variance | 69.563 | 48.958 |
| Standard Deviation | 8.34 | 6.997 |
| Standard Error | 1.37 | 1.65 | t value=5.5587 df=53 p<0.005
The means of the two samples are HIGHLY SIGNIFICANT.

SUMMARY

In the Nicorandil group the patients showed a highly significant increase in penile blood flow provoked by papaverine ($p<0.005$), while placebo did not enhance papaverine induced penile blood flow ($p=1$).

When papaverine induced penile blood flow velocity was compard between Nicorandil and placebo group, Nicorandil showed a statistically significant increase over placebo ($p<0.005$).

TABLE 1

CHANGES IN THE PENILE BLOOD FLOW VELOCITY IN THE TREATED GROUP

| | Penile Blood Flow Velocity (cm/sec) | | | | | |
|---|---|---|---|---|---|---|
| | Pre Treatment | | | Post Treatment | | |
| | Basal | Papaverine induced peak | Percent increase | Basal | Papaverine induced peak | Percent increase |
| NICORANDIL GROUP n = 37 | 8.2 | 20.3 | 147.56 | 7.9 | 21.3 | 169.62 |
| | 12.6 | 28.5 | 126.19 | 12.5 | 36.2 | 189.60 |
| | 11.7 | 23.7 | 102.56 | 11.2 | 35.8 | 219.64 |
| | 16.1 | 31.5 | 95.65 | 15.8 | 49.3 | 212.03 |
| | 15.3 | 27.9 | 82.35 | 15.3 | 29.3 | 91.5 |
| | 15.8 | 33.6 | 112.66 | 15.3 | 54.2 | 254.25 |
| | 17.3 | 31.9 | 84.39 | 17.0 | 66.0 | 288.24 |
| | 16.3 | 26.8 | 64.42 | 16.6 | 32.9 | 98.19 |
| | 13.6 | 31.2 | 129.41 | 13.5 | 39.9 | 195.56 |
| | 12.9 | 25.7 | 99.22 | 12.7 | 41.2 | 231.15 |
| | 14.1 | 30.6 | 117.02 | 14.6 | 48.3 | 230.82 |
| | 15.6 | 36.7 | 135.26 | 15.1 | 53.2 | 252.32 |
| | 12.6 | 28.3 | 124.60 | 12.3 | 41.2 | 234.96 |
| | 13.3 | 30.6 | 130.08 | 13.0 | 44.20 | 240.00 |
| | 15.3 | 30.9 | 101.96 | 15.8 | 47.1 | 198.10 |
| | 17.3 | 29.7 | 71.68 | 17.0 | 49.2 | 189.41 |
| | 14.7 | 39.2 | 166.67 | 14.6 | 45.0 | 208.22 |
| | 10.3 | 23.7 | 130.10 | 10.3 | 32.8 | 218.45 |
| | 16.53 | 40.0 | 142.42 | 16.3 | 52.3 | 220.86 |
| | 12.1 | 25.7 | 112.40 | 12.5 | 49.3 | 294.40 |
| | 12.8 | 31.9 | 149.22 | 12.7 | 43.2 | 240.16 |
| | 12.5 | 27.9 | 123.20 | 12.3 | 39.3 | 219.51 |
| | 15.3 | 34.9 | 128.10 | 15.1 | 47.9 | 217.22 |
| | 18.3 | 43.2 | 136.07 | 18.1 | 60.4 | 233.70 |
| | 18.1 | 39.1 | 116.02 | 18.6 | 56.3 | 202.69 |
| | 12.7 | 30.0 | 136.22 | 12.5 | 39.2 | 213.60 |
| | 17.3 | 42.3 | 144.51 | 17.1 | 56.4 | 229.82 |
| | 15.6 | 32.7 | 109.62 | 15.5 | 47.1 | 203.87 |
| | 19.7 | 53.2 | 170.05 | 19.5 | 67.5 | 246.15 |
| | 17.3 | 40.2 | 132.37 | 17.3 | 61.9 | 257.80 |
| | 16.3 | 35.0 | 114.72 | 16.7 | 52.1 | 211.98 |
| | 12.9 | 29.5 | 128.68 | 13.3 | 43.2 | 224.81 |
| | 13.9 | 29.5 | 112.23 | 13.5 | 41.2 | 205.19 |
| | 14.3 | 38.6 | 169.93 | 14.2 | 45.3 | 219.01 |
| | 15.9 | 42.3 | 166.04 | 15.7 | 61.3 | 290.45 |
| | 14.6 | 37.2 | 154.79 | 14.5 | 45.6 | 214.48 |
| | 15.2 | 42.3 | 178.29 | 15.5 | 52.1 | 236.13 |
| Mean | 14.71 | 33.14 | 125.59 | 14.63 | 46.75 | 219.02 |
| Standard Deviation | 2.368 | 6.79 | 27.00 | 2.40 | 10.09+-- | 40.01 |
| Standard Error | 0.39 | 1.12 | 4.44 | 0.39 | 1.66 | 6.58 |

TABLE 2

CHANGES IN THE PENILE BLOOD FLOW VELOCITY IN THE PLACEBO GROUP

| | Penile Blood Flow Velocity (cm/sec) | | | | | |
|---|---|---|---|---|---|---|
| | Pre Treatment | | | Post Treatment | | |
| | Basal | Papaverine induced peak | Percent increase | Basal | Papaverine induced peak | Percent increase |
| PLACEBO GROUP n = 18 | 13.7 | 29.3 | 113.87 | 13.5 | 32.1 | 137.78 |
| | 17.6 | 43.2 | 145.45 | 17.9 | 41.6 | 132.40 |
| | 11.7 | 30.1 | 157.36 | 11.7 | 29.7 | 153.85 |
| | 14.3 | 36.9 | 158.04 | 14.5 | 35.8 | 146.90 |
| | 15.3 | 52.1 | 240.52 | 15.2 | 52.6 | 246.05 |
| | 8.2 | 20.6 | 151.22 | 8.1 | 21.3 | 162.96 |
| | 18.3 | 34.5 | 88.52 | 18.3 | 36.2 | 97.81 |
| | 18.3 | 32.7 | 78.69 | 18.0 | 31.8 | 76.67 |
| | 12.9 | 30.0 | 132.56 | 12.5 | 31.2 | 149.60 |
| | 10.9 | 23.7 | 117.43 | 10.8 | 23.1 | 113.89 |
| | 16.2 | 40.9 | 152.47 | 16.0 | 48.3 | 201.88 |
| | 7.9 | 21.4 | 170.89 | 7.7 | 23.2 | 201.30 |
| | 8.3 | 20.1 | 142.17 | 8.1 | 21.3 | 162.96 |
| | 18.3 | 32.8 | 79.23 | 18.2 | 31.7 | 74.18 |
| | 20.3 | 42.3 | 108.37 | 19.7 | 41.6 | 111.17 |

TABLE 2-continued

CHANGES IN THE PENILE BLOOD FLOW VELOCITY IN THE PLACEBO GROUP

| | Penile Blood Flow Velocity (cm/sec) | | | | | |
|---|---|---|---|---|---|---|
| | Pre Treatment | | | Post Treatment | | |
| | Basal | Papaverine induced peak | Percent increase | Basal | Papaverine induced peak | Percent increase |
| | 9.6 | 25.3 | 163.54 | 9.5 | 26.1 | 174.74 |
| | 11.7 | 27.8 | 137.61 | 11.5 | 26.5 | 130.43 |
| | 13.6 | 43.2 | 217.65 | 13.5 | 41.7 | 208.89 |
| Mean | 13.73 | 33.16 | 141.98 | 13.59 | 33.09 | 149.08 |
| Standard Deviation | 3.89 | 8.78 | 41.42 | 3.88 | 9.19 | 45.02 |
| Standard Error | 0.92 | 2.07 | 9.77 | 0.92 | 2.17 | 10.62 |

Internationally, nicorandil is available in 10 mg strength and the therapeutic dose used for angina is 10 mg daily. The dose used in the current study i.e., 5 mg, twice daily by oral route for 14 days is sub therapeutic for anti angina use. However, it is found to be effective for erectile dysfunction. When administered orally, it is absorbed rapidly and completely from the small intestine. Peak plasma levels occur around one hour after oral administration which corresponds to its peak hemo-dynamic effects. This steady state plasma concentration of nicorandil is usually reached after four days of continuous administration. Since nicorandil does not undergo significant hepatic first pass metabolism, oral administration does not handicap its efficacy unlike phentolamine.

The present invention takes advantage of the fact that nicorandil does not get significantly metabolised through its first passage through liver. Being a potent arteriolar dilator, nicorandil can induce a fall in blood pressure by decreasing systemic vascular resistance. Such fall of blood pressure can by reflex action stimulate the sympathetic nervous system and affect erectile function. Therefore, an optimum dosage required to produced improved erectile function without adverse hemo-dynamic impact was hitherto unknown. Initial pilot studies by the present inventors indicate excellent results with 5 mg dose of nicorandil which appears to be optimum to improve erectile function without significant drop of blood pressure of patients in question.

It has also been observed that a 10 mg dose is prone to induce headache in almost 36.4% patients. The incidence of headache was found to be quite rare with a dose of 5 mg and therefore, chances of such dosage affecting the psychogenic aspects of sexual function are rare.

Apart from the convenience of non-invasive route of administration, nicorandil reaches a steady—state level within four days of oral administration. This precludes the anticipatory use of nicorandil by sexually active males. In such cases, sub lingual route will be the preferred mode of administration. However, sub lingual use could produce significant drop in blood pressure with a reflex tachycardia and therefore, the dose needs to be individualised in each patient.

The minimum therapeutic dose of nicorandil required for its ischaemic action is 10 mg, twice daily. In some patients it can be started in the dose of 5 mg twice daily to be increased up to 30 mg twice daily. Thus, 5 mg twice daily can be considered sub therapeutic. The effects of nicorandil on myocardial tissue depend on the presence of ischaemic myocardium. On non-ischaemic myocardium, nicorandil has no effect at therapeutic doses. Therefore, the present invention applies to only patients of vasogenic erectile function.

What is claimed is:

1. A method of treating a mammal with penile erectile dysfunction or female sexual arousal dysfunction which comprises administering orally, sublingually or bucally to said mammal in need of such treatment an effective amount of the compound of formula (I)

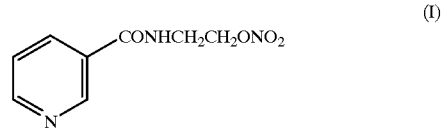

a pharmaceutically acceptable salt thereof, a composition comprising the compound of formula (I) and a physiologically acceptable diluent, carrier or excipient, or a composition comprising a pharmaceutically acceptable salt of the compound of formula (I) and a physiologically acceptable diluent, carrier or excipient.

2. A method of treating a mammal to improve penile erection function or female sexual function which comprises administering orally, sublingually or bucally to said mammal in need of such treatment an effective amount of the compound of formula (I)

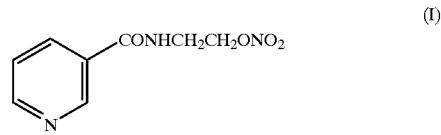

a pharmaceutically acceptable salt thereof, a composition comprising the compound of formula (I) and a physiologically acceptable diluent, carrier or excipient, or a composition comprising a pharmaceutically acceptable salt of the compound of formula (I) and a physiologically acceptable diluent, carrier or excipient.

3. The method according to claim 1, wherein the compound of formula (I)

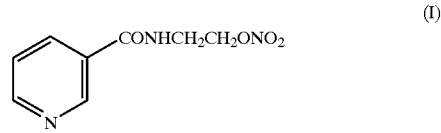

a pharmaceutically acceptable salt thereof, a composition comprising the compound of formula (I) and a physiologically acceptable diluent, carrier or excipient, or a composition comprising a pharmaceutically acceptable salt of the compound of formula (I) and a physiologically acceptable diluent, carrier or excipient is administered orally on a periodic basis.

4. The method according to claim 2, wherein the compound of formula (I)

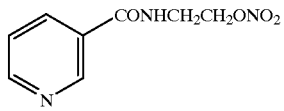

a pharmaceutically acceptable salt thereof, a composition comprising the compound of formula (I) and a physiologically acceptable diluent, carrier or excipient or a composition comprising a pharmaceutically acceptable salt of the compound of formula (I) and a physiologically acceptable diluent, carrier or excipient is administered orally on a periodic basis.

5. A method for preventing penile erecticle dysfunction or female sexual arousal dysfunction in a mammal which comprises administering orally a prophylactically effective amount of the compound of formula (I)

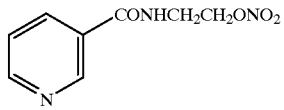

a pharmaceutically acceptable salt thereof, a composition comprising the compound of formula (I) and a physiologically acceptable diluent, carrier or excipient, or a composition comprising a pharmaceutically acceptable salt of the compound of formula (I) and a physiologically acceptable diluent, carrier or excipient.

6. A method for preventing penile erecticle dysfunction or female sexual arousal dysfunction in a mammal which comprises administering sublingually a prophylactically effective amount of the compound of formula (I)

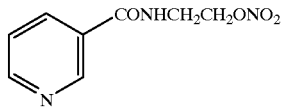

a pharmaceutically acceptable salt thereof, a composition comprising the compound of formula (I) and a physiologically acceptable diluent, carrier or excipient, or a composition comprising a pharmaceutically acceptable salt of the compound of formula (I) and a physiologically acceptable diluent, carrier or excipient.

7. A method of treating a mammal with penile erectile dysfunction or female sexual arousal dysfunction which comprises topically applying to said mammal in need thereof an effective amount of the compound of formula (I)

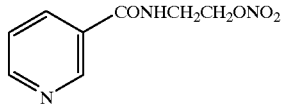

a pharmaceutically acceptable salt thereof, a composition comprising the compound of formula (I) and a physiologically acceptable diluent, carrier or excipient, or a composition comprising a pharmaceutically acceptable salt of the compound of formula (I) and a physiologically acceptable diluent, carrier or excipient.

8. A method of treating a mammal to improve penile erection function or female sexual function which comprises applying topically to said mammal in need thereof an effective amount of the compound of formula (I)

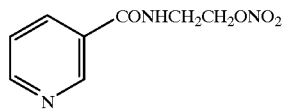

a pharmaceutically acceptable salt thereof, a composition comprising the compound of formula (I) and a physiologically acceptable diluent, carrier or excipient, or a composition comprising a pharmaceutically acceptable salt of the compound of formula (I) and a physiologically acceptable diluent, carrier or excipient.

9. The method of claim 1, wherein the mammal is a human.

10. The method of claim 2, wherein the mammal is a human.

11. The method of claim 7, wherein the mammal is a human.

12. The method of claim 8, wherein the mammal is a human.

13. The method of claim 1, wherein the amount of the compound of formula (I) or the pharmaceutically acceptable salt is 5 to 20 mg.

14. The method of claim 2, wherein the amount of the compound of formula (I) or the pharmaceutically acceptable salt is 5 to 20 mg.

15. The method of claim 3, wherein the amount of the compound of formula (I) or the pharmaceutically acceptable salt is 5 to 20 mg.

16. The method of claim 4, wherein the amount of the compound of formula (I) or the pharmaceutically acceptable salt is 5 to 20 mg.

17. The method of claim 5, wherein the amount of the compound of formula (I) or the pharmaceutically acceptable salt is 5 to 20 mg.

18. The method of claim 6, wherein the amount of the compound of formula (I) or the pharmaceutically acceptable salt is 5 to 20 mg.

19. The method of claim 7, wherein the amount of the compound of formula (I) or the pharmaceutically acceptable salt is 5 to 20 mg.

20. The method of claim 8, wherein the amount of the compound of formula (I) or the pharmaceutically acceptable salt is 5 to 20 mg.

21. The method of claim 5, wherein the mammal is a human.

22. The method of claim 6, wherein the mammal is a human.

* * * * *